United States Patent [19]

McAleer et al.

[11] 4,147,772

[45] Apr. 3, 1979

[54] VACCINE STABILIZER

[75] Inventors: William J. McAleer, Ambler; Henry Z. Markus, Wyncote, both of Pa.

[73] Assignee: Merck & Co., Inc., Rahway, N.J.

[21] Appl. No.: 880,667

[22] Filed: Feb. 23, 1978

Related U.S. Application Data

[63] Continuation-in-part of Ser. No. 654,837, Feb. 3, 1976, abandoned.

[51] Int. Cl.$^2$ .................. A61K 39/12; A61K 39/20; A61K 39/16; A61K 39/34
[52] U.S. Cl. .................................................. 424/89
[58] Field of Search .................... 424/89; 195/1.1–1.8

[56] References Cited

U.S. PATENT DOCUMENTS

| | | | |
|---|---|---|---|
| 2,879,202 | 3/1959 | Alston et al. | 424/89 |
| 2,946,724 | 7/1960 | Valentine | 424/89 |
| 3,133,861 | 5/1964 | Schwarz | 424/89 |
| 3,143,470 | 8/1964 | Wilner | 424/89 |
| 3,156,620 | 11/1969 | Sharpless | 424/89 |
| 3,214,340 | 10/1965 | Laurence | 424/89 |
| 3,322,632 | 5/1967 | Schwick et al. | 424/89 X |
| 3,422,188 | 1/1969 | Cabasso | 424/89 |
| 3,629,399 | 12/1971 | Maulor et al. | 424/89 |
| 3,783,098 | 1/1974 | Calnek et al. | 424/89 X |
| 3,880,993 | 4/1975 | Gilker | 424/89 |

OTHER PUBLICATIONS

Chem. Abstr. 80 #41031f (1974) of Japan 73, 10,523, Apr. 1973.
Chem. Abstr. 76 #144799j (1972) of Fr. M 7773, Mar. 1970.
Chem. Abstr. 67 #42097a (1967) of Faibich. Zh. Mikrobiol. Epidemiol. Immunobiol. 44 (4):69–72 (1967).

*Primary Examiner*—Shep K. Rose
*Attorney, Agent, or Firm*—Donald J. Perrella; Julian S. Levitt

[57] ABSTRACT

A stabilized lyophlized or liquid live viral vaccine contains a live virus, partially hydrolyzed gelatin, a 6-carbon polyhydric alcohol, Medium 199 and acidic buffer.

10 Claims, No Drawings

4,147,772

VACCINE STABILIZER

RELATED APPLICATION

This application is a continuation-in-part of copending application Ser. No. 654,837 filed Feb. 3, 1976, now abandoned.

BACKGROUND OF THE INVENTION

The present invention relates to liquid and lyophilized viral vaccines. More particularly it relates to a stabilizer for liquid and lyophilized viral vaccines.

Due to the worldwide distribution of vaccines and the diversity of ambient temperatures, there has been a need to stabilize these preparations for transportation and use. Several stabilization methods have been used in the past.

(a) Low temperatures (−10° C. to −70° C.). The need for low temperature storage facilities which are not always available limits the practicality of this approach.

(b) Lyophilization Although lyophilization suffers the disadvantages of being an expensive procedure, lyophilized vaccines are reasonably stable and are stored at 4°–8° C. until needed. During this storage period, however, the vaccines slowly deteriorates until after about 12–24 months it does not have sufficient titer to confer immunization. Furthermore, since the lyophilized vaccine must be reconstituted prior to use, the liquid reconstituted preparation loses potency while standing at room temperature. This can result in insufficient titer to confer immunity and results in failure of immunization program.

(c) Stabilizers These are chemical compounds added to the vaccine and are used in conjunction with either lower temperature storage or lyophilization methods. While chemical stabilizers, e.g., $MgSO_4$, SPGA (a stabilizer described by Bovarnick et al., J. Bact. 59:509-522 (1950), the disclosure of which is incorporated herein by reference) and the like are described in the prior art, none imparts the desired enhanced sustained level of stability. The mixture contained 0.218 M sucrose, 0.0038 M monopotassium phosphate, 0.0072 M dipotassium phosphate, 0.0049 M monosodium glutamate, and 1% bovine albumin powder) and the like are described in the prior art, none imparts the desired enhanced sustained level of stability.

OBJECTS OF THE INVENTION

It is, accordingly, an object of the present invention to provide an improved chemical stabilizer for lyophilized and liquid viral vaccines.

Another object is to provide a method for stabilizing lyophilized and liquid viral vaccines.

A further object is to provide lyophilized and liquid viral vaccines having prolonged storage stability with diminished reduction in titer.

These and other objects of the present invention will be apparent from the following description.

SUMMARY OF THE INVENTION

An improved stabilized liquid or lyophilized live viral vaccine contains a live virus, partially hydrolyzed gelatin, a 6-carbon polyhydric alcohol, a cell culture medium, and sufficient physiologically acceptable acidic buffer to maintain the pH at 6.0–6.5.

DETAILED DESCRIPTION

The present invention is directed to a stabilized vaccine composition in lyophilized or liquid form containing a live virus, partially hydrolyzed gelatin, a 6-carbon polyhydric alcohol, a cell culture medium and sufficient physiologically acceptable acidic buffer to maintain the pH at from about 6.0 to about 6.5. Examples of live virus are measles, mumps or rubella, varicella, polio, or hepatitis and the like, or a combination of any two or more of such viruses. Hydrolyzed gelatin is employed to provide a soluble, nongelling proteinaceous matrix with little or no pyrogenicity or antigenicity.

By partially hydrolyzed gelatin is meant gelatin which has been subjected to partial hydrolysis to yield a partially hydrolyzed gelatin having a molecular weight of about 3,000. This gelatin hydrolysis product has approximately the same amino acid composition as gelatin. Unlike gelatin which forms gels but is insoluble in cold water, hydrolyzed gelatin does not gel but is soluble in cold water, and other common liquids such as milk and orange juice. Aqueous solutions containing up to about 10% hydrolyzed gelatin do not increase appreciably in viscosity. Above about 10% concentration, viscosity increases slowly. At about 50% concentration, solutions are quite viscous. The typical amino-acid composition of hydrolyzed gelatin follows:

| | |
|---|---|
| Alanine | 8.5% |
| Arginine | 7.9% |
| Aspartic Acid | 5.7% |
| Cystine | 0.08% |
| Glutamic Acid | 9.5% |
| Glycine | 22.8% |
| Histidine | 0.77% |
| Hydroxy Proline | 13–14% |
| Isoleucine | 1.3% |
| Leucine | 2.9% |
| Lysine | 4.2% |
| Methionine | 0.78% |
| Phenyl Alanine | 2.0% |
| Proline | 13.8% |
| Serine | 3.3% |
| Threonine | 1.9% |
| Tyrosine | 0.40% |
| Valine | 2.4% |

Partially hydrolyzed gelatin may be obtained by enzymatic hydrolysis of gelatin by means of a proteolytic enzyme, such as, for example, papain, chymopapain and bromelin, although other known hydrolysis means may be employed, e.g. acid hydrolysis. A suitable hydrolyzed gelatin is obtainable from Wilson and Co., Inc., Calumet City, Illinois under the trade name SOL-U-PRO. The 6-carbon polyhydric alcohol may be, for example, sorbitol, mannitol or dulcitol. Sorbitol is preferred.

The acidic buffer may be any physiologically acceptable buffer which will maintain the desired pH of from about 6 to about 6.5, for example, phosphate buffer, acetate buffer or citrate buffer. Phosphate buffer is preferred. The stabilizer is diluted with from about 3 to about 8 times, preferably about 5.5 times, its weight of distilled water before use.

By a cell culture medium is meant a nutrient medium which permits growth of cells in vitro. Some specific nutrient media are, for example, Medium 199, Morgan et al., Proc. Soc. Exp. Biol. & Med., 73:1-8, 1950; Basal Medium Eagle, Eagle, Science, 122, 501-504, 1955; In Vitro, Vol. 6, No. 2, 1970; Dulbecco's Modified Eagle's Medium, Dulbecco et al., Virology, 8, 396, 1959; Smith et al., J. Virol., 12, 185-196, 1960; In Vitro, Vol. 6, No. 2, 1970; Minimum Essential Medium (Eagle), Science, 130, 432 (1959) and RPMI Media, Moore et al., 199, 519-524, 1967; In Vitro, Vol. 6, No. 2, 1970.

The stabilizer composition of the present invention contains the following ingredients in about the amounts indicated:

| Ingredient | Parts by weight |
|---|---|
| Partially hydrolyzed gelatin | 2 – 5 |
| Polyhydric alcohol | 2 – 55 |
| Nutrient medium (solids) | 0.5 – 1.7 |
| Physiologically acceptable buffer to adjust pH to 6.0 – 6.5 | quantity sufficient |

With a liquid vaccine sorbitol is generally present in an amount toward the upper end of the range, while with a lyophilized vaccine sorbitol is generally present in an amount toward the lower end of the range.

Specific formulations for the viral vaccine stabilizer of the present invention follow. Formulation B is preferred for a lyophilized vaccine.

| | A | B |
|---|---|---|
| Partially hydrolyzed gelatin | 35.7 g. | 35.7 g. |
| Sorbitol | 526 g. | 35.7 g. |
| Medium 199 | 11.06 g. | 11.06 g. |
| Sodium phosphate buffer, 1 M, pH 6.0 | 100 ml | 100 ml |
| Distilled water | to 1 liter | to 1 liter |

In addition the stabilizer optionally but preferably contains a small amount of $NaHCO_3$ and of phenol red. In the case of the foregoing formulation the $NaHCO_3$ may be present in an amount of about 1.2 g and the phenol red in an amount of about 0.01 g. While particular formulations have been described above it is to be understood that variations in ratios and concentration of each ingredient are contemplated. One volume of bulk vaccine is usually diluted with from about 2 to about 12 volumes of stabilizer.

The following examples illustrate the present invention without, however, limiting the same thereto.

EXAMPLE 1

80 Ml. of measles viral concentrate which has been stored at −70° is thawed in a water bath at 25° C. and then kept at 4°-8°. The liquid viral concentrate is then split into two aliquots each 40 ml.

(a) One 40 ml aliquot from this virus fluid is diluted in 210 ml of the previously described sterile stabilizer of formulation B. Formulation is carried on under aseptic conditions and laminar flow hood. To prevent microbial growth 10.5 mg. Neomycin are added to the preparation. The diluted vaccine is dispensed into 2 ml glass ampules (0.7 ml vaccine per ampule) which are immediately flame sealed and stored at 4°-8° C.

(b) The second 40 ml aliquot is handled as the first, except that, instead of the stabilizer of formulation B, a standard commercial vaccine diluent (SPGA) is used. The storage stability of the vaccines is described in the following table:

| | Titers[1] of Liquid Vaccines Stored at 2-8° C. | |
|---|---|---|
| Time | Stabilizer of Formulation B | SPGA Stabilizer |
| 0 | 3.4 | 3.6 |
| 4 months | 3.2 | 0.6 |

[1]Titers are expressed as $TCID_{50}/0.1$ ml.

EXAMPLE 2

32 Ml. of measles viral concentrate which has been stored at −70° is thawed in a water bath at 25° C. and then kept at 4°-8°. The liquid viral concentrate is then split into two aliquots each 16 ml.

(a) One 16 ml aliquot from this virus fluid is diluted in 48 ml of the previously described sterile stabilizer of formulation B. Formulation is carried on under aseptic conditions and laminar flow hood. To prevent microbial growth 2.5 mg Neomycin are added to the preparation. The diluted vaccine is dispensed into 2 ml glass ampules (0.7 ml vaccine per ampule) which are immediately flame sealed and stored at 37° C.

(b) The second 16 ml aliquot is handled as the first, except that, instead of the stabilizer of formulation B, the stabilizer of formulation A is used. The storage stability of the vaccines is described in the following table:

| | Titers[1] of Liquid Vaccines Stored at 37° C. | |
|---|---|---|
| Time | Stabilizer of Formulation B | Stabilizer of Formulation A |
| 0 | 2.9 | 2.7 |
| 24 Hours | 1.6 | 2.1 |
| 48 Hours | 1.2 | 1.8 |
| 72 Hours | 0.6 | 1.4 |

[1]Titers are expressed as $TCID_{50}/0.1$ ml.

EXAMPLE 3

80 Ml. of measles viral concentrate which has been stored at −70° C. is thawed in a water bath at 20° C. and then kept at 4°-8° C. The liquid viral concentrate is split into two parts of 40 ml each.

(a) One 40 ml aliquot from ths virus fluid is diluted in 210 ml of the previously described sterile stabilizer of formulation B. Formulation is carried on under aseptic conditions and laminar flow hood. To prevent microbial growth 10.5 mg Neomycin are added to the preparation. The diluted vaccine is dispensed into 3 ml glass vials (0.7 vaccine per vial) which are lyophilized, stoppered and stored at 37° C.

(b) The second 40 ml viral aliquot is handled as the first one, except that, instead of the stabilizer of formulation B, a standard commercial diluent (Medium 199 containing SPGA) is used.

The storage stability of these vaccines is described in the following table:

| | Titers[1] of Lyophilized Vaccine Stored at 37° C. | |
|---|---|---|
| Time | Stabilizer of Formulation B | SPGA Stabilizer |
| 0 | 3.5 | 3.5 |
| 7 days | 3.6 | 0.6 |

[1]Titers are expressed as log $TCID_{50}/0.1$ ml.

EXAMPLE 4

Lyophilized vials prepared as in Example 3 are reconstituted in distilled water (0.7 ml per vial) and stored at 2°–8° C.

The storage stability of these vaccines is described in the following table:

| Time | Titers[1] of Reconstituted Vaccine Stored at 2–8° C. | |
|---|---|---|
| | Stabilizer of Formulation B | SPGA Stabilizer |
| 0 | 3.70 | 3.43 |
| 4 days | 3.17 | 2.20 |
| 1 week | 3.23 | 2 |
| 8 weeks | 3.03 | — |
| Loss (log/week) | 0.030 | 0.649 |

[1]Titers are expressed as log $TCID_{50}/0.1$ ml.

What is claimed is:

1. A vaccine comprising an inactivated or attenuated virus and a stabilizer consisting essentially of on a parts by weight basis from about 2 to about 5 parts partially hydrolyzed gelatin having a molecular weight of about 3,000, from about 2 to about 55 parts of sorbitol, mannitol or dulcitol, from about 0.5 to about 1.7 parts of Medium 199 or equivalent cell culture medium and an amount of a physiologically acceptable acidic buffer effective to adjust the pH to from about 6.0 to about 6.5.

2. A vaccine according to claim 1 wherein the 6-carbon polyhydric alcohol is sorbitol.

3. A vaccine according to claim 1 wherein the buffer is phosphate buffer.

4. A vaccine according to claim 1 wherein the virus is measles, mumps, rubella, varicella, polio or hepatitis, herpes simplex 1, herpes simplex 2, or combinations thereof.

5. A vaccine according to claim 1 wherein the stabilizer consists essentially of on a parts by weight basis about 3.6 parts of partially hydrolyzed gelatin, about 3.6 parts of sorbitol, about 1.1 parts of Medium 199 and an amount of phosphate buffer effective to adjust the pH to from about 6.0 to about 6.5.

6. A vaccine according to claim 1 wherein the stabilizer consists essentially on a parts by weight basis about 3.6 parts of partially hydrolyzed gelatin, about 53 parts of sorbitol, about 1.1 parts of Medium 199 and an amount of phosphate buffer effective to adjust the pH to from about 6.0 to about 6.5.

7. A stabilized vaccine obtained by reconstituting a lyophilized vaccine containing a stabilizer according to claim 1.

8. A stabilized vaccine obtained by thawing a frozen vaccine containing a stabilizer according to claim 1.

9. A vaccine according to claim 1 containing from about 2 to about 12 volumes of stabilizer to about one volume of vaccine.

10. A method for stabilizing a vaccine comprising adding to the vaccine an amount of stabilizer according to claim 1 effective to stabilize the vaccine.

* * * * *